United States Patent
Vitaris

(10) Patent No.: US 9,913,757 B2
(45) Date of Patent: Mar. 13, 2018

(54) VACUUM WOUND THERAPY WOUND DRESSING WITH VARIABLE PERFORMANCE ZONES

(71) Applicant: Smith & Nephew Inc., Memphis, TN (US)

(72) Inventor: Ronald F. Vitaris, Worcester, MA (US)

(73) Assignee: Smith & Nephew, Inc., Memphis, TN (US)

( * ) Notice: Subject to any disclaimer, the term of this patent is extended or adjusted under 35 U.S.C. 154(b) by 24 days.

(21) Appl. No.: 14/927,109

(22) Filed: Oct. 29, 2015

(65) Prior Publication Data
US 2016/0045374 A1 Feb. 18, 2016

Related U.S. Application Data

(63) Continuation of application No. 12/047,910, filed on Mar. 13, 2008, now abandoned.

(51) Int. Cl.
*A61M 1/00* (2006.01)
*A61F 13/00* (2006.01)
(Continued)

(52) U.S. Cl.
CPC .. *A61F 13/00068* (2013.01); *A61F 13/00063* (2013.01); *A61F 13/022* (2013.01);
(Continued)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS 4,969,880 A 11/1990 Zamierowski
4,997,438 A 3/1991 Nipper
(Continued)

FOREIGN PATENT DOCUMENTS

CN 1438904 A 8/2003
GB 1521171 8/1978
(Continued)

OTHER PUBLICATIONS

U.S. Appl. No. 12/047,910, filed Mar. 13, 2008, 2009/0234306.

*Primary Examiner* — Tatyana Zalukaeva
*Assistant Examiner* — Ilya Treyger
(74) *Attorney, Agent, or Firm* — Knobbe, Martens, Olson & Bear LLP

(57) ABSTRACT

A dressing for an open wound includes a cover layer dimensioned for positioning relative to a wound bed. The cover layer permits an evacuation of the space around the wound bed such that a sub-atmospheric pressure may be established to stimulate healing and facilitate the removal of fluid from the wound. Multiple performance zones in the cover layer allow the wound dressing to remain in position through repeated cycles of evacuation without placing undue strain on the wound bed. An outer peripheral zone may include a high peal-strength adhesive while an intermediate zone may include a shear resistant adhesive. A central zone may be devoid of any coating to maximize moisture transmission through cover layer.

12 Claims, 4 Drawing Sheets

(51) Int. Cl.
*A61F 13/02* (2006.01)
*A61M 13/00* (2006.01)
*A61M 27/00* (2006.01)
*A61B 17/50* (2006.01)

(52) U.S. Cl.
CPC ........ *A61F 13/025* (2013.01); *A61F 13/0206* (2013.01); *A61F 13/0213* (2013.01); *A61F 13/0216* (2013.01); *A61F 13/0226* (2013.01); *A61F 13/0243* (2013.01); *A61F 13/0253* (2013.01); *A61F 13/0256* (2013.01); *A61F 2013/0054* (2013.01); *A61F 2013/00174* (2013.01); *A61F 2013/00217* (2013.01); *A61F 2013/00246* (2013.01); *A61F 2013/00263* (2013.01); *A61F 2013/00285* (2013.01); *A61F 2013/00536* (2013.01); *A61F 2013/00646* (2013.01); *A61F 2013/00804* (2013.01); *A61F 2013/00855* (2013.01); *A61F 2013/00902* (2013.01)

(56) References Cited

U.S. PATENT DOCUMENTS

| | | | |
|---|---|---|---|
| 5,100,396 A | | 3/1992 | Zamierowski |
| 5,106,629 A | | 4/1992 | Cartmell et al. |
| 5,176,663 A | | 1/1993 | Svedman et al. |
| 5,261,893 A | | 11/1993 | Zamierowski |
| 5,527,293 A | | 6/1996 | Zamierowski |
| 5,549,584 A | | 8/1996 | Gross |
| 5,578,317 A | * | 11/1996 | Mulder ............ A61F 13/00063 424/443 |
| 5,636,643 A | | 6/1997 | Argenta et al. |
| 5,645,081 A | | 7/1997 | Argenta et al. |
| 5,678,564 A | | 10/1997 | Lawrence et al. |
| 5,701,917 A | | 12/1997 | Khouri |
| 5,830,496 A | | 11/1998 | Freeman |
| 5,911,222 A | | 6/1999 | Lawrence et al. |
| 6,117,111 A | | 9/2000 | Fleischmann |
| 6,135,116 A | | 10/2000 | Vogel et al. |
| 6,345,623 B1 | | 2/2002 | Heaton et al. |
| 6,348,423 B1 | | 2/2002 | Griffiths et al. |
| 6,488,643 B1 | | 12/2002 | Tumey et al. |
| 6,562,014 B2 | | 5/2003 | Lin et al. |
| 6,607,495 B1 | | 8/2003 | Skalak et al. |
| 6,626,891 B2 | | 9/2003 | Ohmstede |
| 6,695,824 B2 | | 2/2004 | Howard et al. |
| 6,752,794 B2 | | 6/2004 | Lockwood et al. |
| 6,767,334 B1 | | 7/2004 | Randolph |
| 6,824,533 B2 | | 11/2004 | Risk, Jr. et al. |
| 6,855,135 B2 | | 2/2005 | Lockwood et al. |
| 6,979,324 B2 | | 12/2005 | Bybordi et al. |
| 7,070,584 B2 | | 7/2006 | Johnson et al. |
| 7,117,869 B2 | | 10/2006 | Heaton et al. |
| 7,128,735 B2 | | 10/2006 | Weston |
| 7,144,390 B1 | | 12/2006 | Hanningan et al. |
| 7,182,758 B2 | | 2/2007 | McCraw |
| 7,195,624 B2 | | 3/2007 | Lockwood et al. |
| 7,198,046 B1 | | 4/2007 | Argenta et al. |
| 7,216,651 B2 | | 5/2007 | Argenta et al. |
| 7,279,612 B1 | | 10/2007 | Heaton et al. |
| 7,338,482 B2 | | 3/2008 | Lockwood et al. |
| 7,700,819 B2 | | 4/2010 | Ambrosio et al. |
| 7,708,724 B2 | | 5/2010 | Weston |
| 7,732,655 B2 | | 6/2010 | Cullen et al. |
| 7,779,625 B2 | | 8/2010 | Joshi et al. |
| 7,896,856 B2 | | 3/2011 | Petrosenko et al. |
| 7,909,805 B2 | | 3/2011 | Weston |
| 8,062,272 B2 | | 11/2011 | Weston |
| 8,282,611 B2 | | 10/2012 | Weston |
| 8,303,552 B2 | | 11/2012 | Weston |
| 8,460,255 B2 | | 6/2013 | Joshi et al. |
| 8,795,243 B2 | | 8/2014 | Weston |
| 9,168,330 B2 | | 10/2015 | Joshi et al. |
| 9,198,801 B2 | | 12/2015 | Weston |
| 9,272,080 B2 | | 3/2016 | Weston |
| 2001/0031943 A1 | | 10/2001 | Urie |
| 2001/0043943 A1 | | 11/2001 | Coffey |
| 2003/0208149 A1 | | 11/2003 | Coffey |
| 2003/0212357 A1 | | 11/2003 | Pace |
| 2003/0212359 A1 | | 11/2003 | Butler |
| 2003/0219469 A1 | | 11/2003 | Johnson et al. |
| 2004/0030304 A1 | | 2/2004 | Hunt et al. |
| 2004/0039415 A1 | | 2/2004 | Zamierowski |
| 2004/0039391 A1 | | 4/2004 | Argenta et al. |
| 2004/0064132 A1 | | 4/2004 | Boehringer et al. |
| 2004/0093026 A1 | | 5/2004 | Weidenhagen et al. |
| 2004/0241213 A1 | | 12/2004 | Bray |
| 2005/0020955 A1 | | 1/2005 | Sanders et al. |
| 2005/0070835 A1 | | 3/2005 | Joshi |
| 2005/0159695 A1 | | 7/2005 | Cullen et al. |
| 2005/0177190 A1 | | 8/2005 | Zamierowski |
| 2005/0182445 A1 | | 8/2005 | Zamierowski |
| 2006/0100586 A1 | | 5/2006 | Karpowicz et al. |
| 2006/0100594 A1 | | 5/2006 | Adams et al. |
| 2006/0116620 A1 | | 6/2006 | Oyaski |
| 2006/0264796 A1 | | 11/2006 | Flick et al. |
| 2007/0014837 A1 | | 1/2007 | Johnson et al. |
| 2007/0021697 A1 | | 1/2007 | Ginther et al. |
| 2007/0027414 A1 | | 2/2007 | Hoffman et al. |
| 2007/0032754 A1 | | 2/2007 | Walsh |
| 2007/0032755 A1 | | 2/2007 | Walsh |
| 2007/0032778 A1 | | 2/2007 | Heaton et al. |
| 2007/0055209 A1 | | 3/2007 | Patel et al. |
| 2007/0166817 A1 | | 7/2007 | Wilkes et al. |
| 2007/0185463 A1 | | 8/2007 | Mulligan |
| 2007/0219532 A1 | | 9/2007 | Karpowicz et al. |
| 2007/0225663 A1 | | 9/2007 | Watt et al. |
| 2007/0260207 A1 | | 11/2007 | Ugander et al. |
| 2007/0260279 A1 | * | 11/2007 | Hotter ................ A61B 17/0401 606/228 |
| 2007/0265585 A1 | | 11/2007 | Joshi et al. |
| 2007/0275077 A1 | | 11/2007 | Arias |
| 2007/0282310 A1 | | 12/2007 | Bengtson et al. |
| 2007/0286942 A1 | | 12/2007 | Wu et al. |
| 2008/0003274 A1 | | 1/2008 | Kaiser |
| 2008/0004559 A1 | | 1/2008 | Riesinger |
| 2008/0033325 A1 | | 2/2008 | Van der Hulst |
| 2008/0039761 A1 | | 2/2008 | Heaton et al. |
| 2008/0139988 A1 | * | 6/2008 | Dayan ............... A61F 13/00034 602/48 |
| 2009/0234306 A1 | | 9/2009 | Vitaris |
| 2009/0299251 A1 | | 12/2009 | Buan |
| 2011/0118683 A1 | | 5/2011 | Weston |
| 2013/0150814 A1 | | 6/2013 | Buan |
| 2013/0274688 A1 | | 10/2013 | Weston |
| 2016/0051737 A1 | | 2/2016 | Joshi et al. |
| 2016/0206790 A1 | | 7/2016 | Weston |
| 2016/0256613 A1 | | 9/2016 | Weston |

FOREIGN PATENT DOCUMENTS

| | | |
|---|---|---|
| WO | WO 2000/42958 | 7/2000 |
| WO | WO 2001/85248 | 11/2001 |
| WO | WO 2006/005939 | 1/2006 |

* cited by examiner

VACUUM WOUND THERAPY WOUND DRESSING WITH VARIABLE PERFORMANCE ZONES

CROSS-REFERENCE TO RELATED APPLICATIONS

This application is a continuation application of U.S. application Ser. No. 12/047,910, filed on Mar. 13, 2008 entitled "VACUUM WOUND THERAPY WOUND DRESSING WITH VARIABLE PERFORMANCE ZONES" which is hereby incorporated herein by reference in its entirety and is to be considered a part of this specification.

BACKGROUND

1. Technical Field

The present disclosure relates generally to a wound dressing for treating an open wound with a vacuum wound therapy treatment. In particular, the disclosure relates to a dressing having a cover layer employing a plurality of zones of variable performance characteristics to promote healing of the wound.

2. Background of Related Art

The body's natural wound healing process is a complex series of events beginning at the moment of injury. Initially the body reacts by delivering proteins and other factors to the wound through the blood stream to minimize the damage. Blood clots to prevent blood loss while cells engulf bacteria and debris to carry it away from the wound site. Next, the body begins to repair itself in a stage of healing often referred to as the proliferate phase. This phase is characterized by the deposition granulation tissue in the wound bed. Granulation tissue provides a base structure over which cells may migrate inwardly from the periphery to close the wound. Finally the process ends as collagen gives strength to new tissue over time often forming a scar.

One technique for promoting the natural healing process, particularly, but not exclusively during the proliferate phase, is known as vacuum wound therapy (VWT). Application of a reduced pressure, e.g. sub-atmospheric, to a localized reservoir over a wound has been found to assist in closing the wound. The reduced pressure may be effective to promote blood flow to the area to stimulate the formation of granulation tissue and the migration of healthy tissue over the wound in the natural process. Also a reduced pressure may assist in removing fluids exuding from the wound, which may inhibit bacterial growth. This technique has proven effective for chronic or non-healing wounds, but has also been used in for other purposes such as post-operative wound care.

The general VWT protocol provides for the introduction of a filler material into the wound to absorb exudates. The filler material may comprise such materials as non-reticulated foams, non-woven fabrics or gauze. The wound and the filler material may then covered by moisture vapor permeable cover layer that permits oxygen exchange with the environment, which may be essential for wound healing. The cover layer often includes an adhesive periphery that forms a substantially fluid tight seal with the healthy skin surrounding the wound. The cover layer thus defines a vacuum reservoir over the wound where a reduced pressure may be maintained over time by individual or cyclic evacuation procedures.

An aspect of concern in a VWT treatment is the management of forces generated in the dressing when a vacuum is applied. Such forces may cause the separation of the dressing from the skin, thereby limiting the effect of the VWT treatment and increasing the probability that microorganisms will infect the wound. Also, such forces may damage newly forming granulation tissue. The application of a vacuum can deform a flexible cover layer such that it compresses the filler and increases its tendency to adhere to the wound bed. Additionally, the deformation of the cover layer creates transverse shear forces along the skin-adhesive interface at the peri-wound area. These shear forces can cause the dressing to shift and/or pull away from the skin where gaps and wrinkles may develop. Such movement, and the mentioned results thereof, can inhibit the dressing's ability to provide a seal that is suitable for both the maintenance of a vacuum and for prohibiting the infiltration of contamination.

Adhesives applied to a cover layer to strengthen or reinforce the dressing's attachment to the skin may diminish the moisture vapor permeability of the dressing affecting its ability to permit oxygen exchange with the environment. Diminished moisture vapor permeability could also lead to the accumulation of moisture at the skin-adhesive interface. Permitting such an accumulation undermines the dressing's adhesion to the skin at the peri-wound area, thereby reducing the wear-time of the dressing, the effectiveness of the treatment and the health of the peri-wound area. Accordingly a need exists for a dressing suitable for use in a VWT procedure.

SUMMARY

The present disclosure describes a dressing for use in a vacuum wound therapy procedure to promote healing of a wound. The dressing includes a cover layer having a plurality of zones of variable performance characteristics. A central zone is defined by a portion of a moisture vapor permeable membrane devoid of any coating that would otherwise inhibit the transmission of moisture through the membrane. A peripheral zone adjacent a periphery of the cover layer is adapted to provide a seal around the perimeter of the wound. At least one intermediate zone is disposed between the central zone and the peripheral zone to impart a therapeutic effect or benefit to the wound.

The peripheral zone may include a high peal-strength adhesive while a first intermediate zone may include a shear-resistant adhesive. A second intermediate zone may include a coating adapted for medicament delivery, a hydrogel for maintaining a moist wound environment, or at least one of an anti-infective agent, an antimicrobial, antibiotic, analgesic, healing factor, vitamins, growth factors, debridement agents or nutrients.

The moisture variable permeable membrane may extend to a periphery of the cover layer so as to constitute a backing layer for the attachment of an adhesive defining the peripheral zone. The peripheral zone and at least one intermediate zone may be arranged concentrically with respect to the central zone. The cover layer may also include a port for permitting access to a vacuum reservoir defined beneath the cover layer for a vacuum tube.

According to another aspect of the disclosure a wound dressing apparatus for use in a vacuum wound therapy procedure includes a contact layer and a filler material positioned in a wound bed and covered by a cover layer. The cover layer defines a vacuum reservoir above the wound bed and permits access of a vacuum tube to the vacuum reservoir. The cover layer includes a peripheral zone to provide a seal around the wound bed, at least one intermediate zone for imparting a therapeutic effect or benefit to the wound bed, and a central zone formed from a moisture vapor permeable membrane.

The contact layer may be formed from a conical apertured film to promote unidirectional flow of exudates from the wound. The absorbent filler material may include polyolefin filaments arranged in a multi-strand bundle. Also, a vacuum system in fluid communication with the vacuum reservoir may include a vacuum source, a collection canister and a one-way valve.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
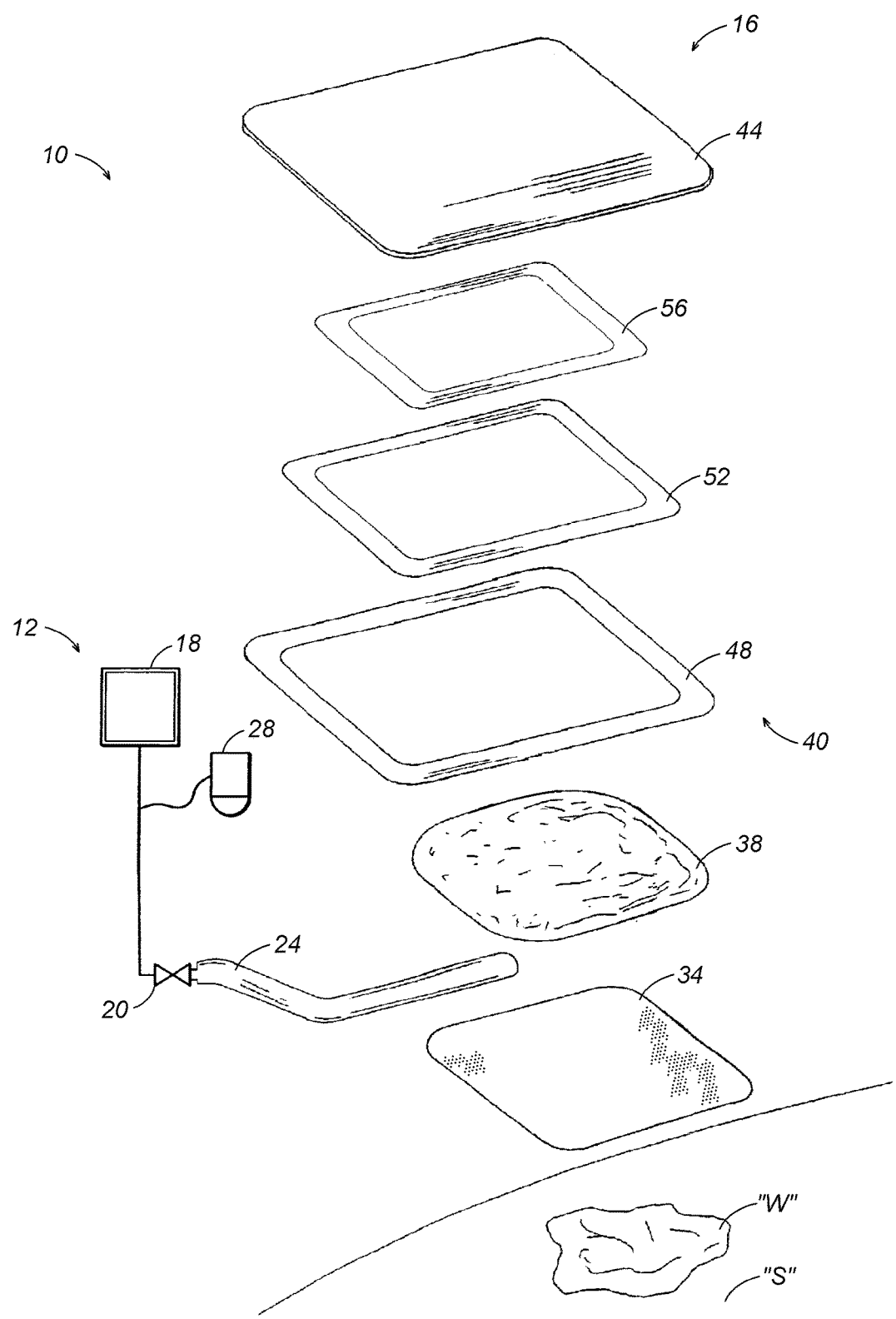
FIG. 1 is an exploded perspective view of a vacuum wound therapy system in accordance with the present disclosure.

The wound dressing of the present disclosure promotes healing of a wound by providing a reservoir over the wound where a reduced pressure may be maintained. The reservoir subjects the wound to a sub-atmospheric pressure to effectively draw wound fluid, including liquid exudates, from the wound without the continuous use of a vacuum pump. Hence, vacuum pressure may be applied once, or in varying intervals depending on the nature and severity of the wound. The use of a wound dressing in this manner has been found to promote healing by reducing the probability of infection, stimulating the deposition of granulation tissue and other beneficial processes. The wound dressing of the present disclosure includes a cover layer having multiple performance zones to enhance the effect of a vacuum wound therapy treatment.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

Referring initially to FIG. 1, a vacuum wound therapy system according to the present disclosure is depicted generally as 10 for use on a wound "w" surrounded by healthy skin "s." The vacuum wound therapy system 10 includes a vacuum system 12 in fluid communication with a vacuum reservoir 14 (FIG. 4A) defined by or within the wound dressing 16. The vacuum system 12 includes a vacuum source 18 coupled to the dressing 16 through a one-way valve 20 and a vacuum tube 24. A collection canister 28 is provided for wound drainage and debris. The vacuum system 12 is adapted to provide a reduced pressure to the vacuum reservoir 14 appropriate to stimulate healing of the wound. A more detailed description of an appropriate vacuum system 12 is found in commonly assigned U.S. Patent Application Publication 2007/0066946, the entire contents of which are incorporated herein by reference.

Figure 3A:
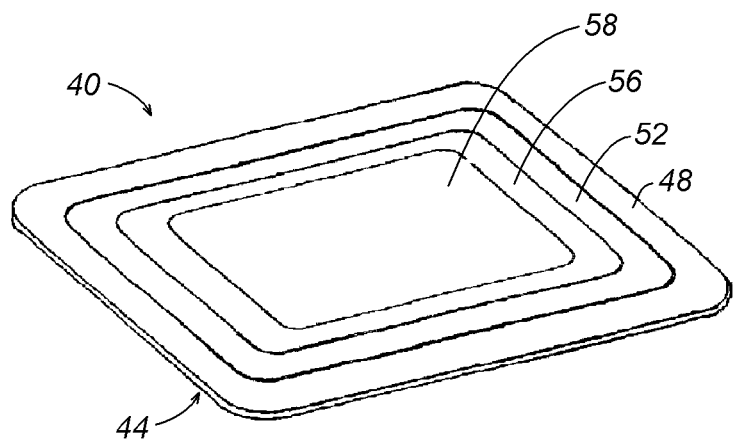
FIG. 3A is a reverse angle perspective view of the cover layer of FIG. 1.

Wound dressing 16 generally includes a contact layer 34, filler 38 and a cover layer 40 defining a plurality of performance zones. A backing layer 44 may be coated with various materials in a juxtaposed relation to define a peripheral zone 48, a first intermediate zone 52, a second intermediate zone 56 and a central zone 58 (FIG. 3A). Alternatively, each zone may comprise an independent layer positioned adjacent the wound bed "w." Each layer is described in greater detail below.

Contact layer 34 may be sufficiently conformable to be positioned in direct contact with an irregularly shaped surface of a wound bed "w." A thin film of polyethylene or other suitable non-adherent material may form the contact layer 34 to limit the adherence of filler 38 and other substances to the wound "w." Apertures or perforations in the film permit fluids to pass through the contact layer 34, allowing for the sub-atmospheric pressure to penetrate into the wound "w" and for exudates to flow freely out of the wound "w." By selecting an appropriate film material, the passage of wound exudate through contact layer 34 may be controlled so as to be substantially unidirectional to prevent wound exudate from flowing back into the wound. To promote a unidirectional flow, a conical apertured film, such as those provided by Tredegar Film Products of Richmond, Va., may be selected for forming contact layer 20. This type of film is arranged with apertures positioned at the peaks of cone shaped formations in the film material such that exudate encounters the film as an array of micro-funnels in one direction and an array of collecting basins in the other. Unidirectional flow of exudates may also be promoted by the selection of other materials including a lamination of layers having varying absorptive characteristics. One exemplary material, which may be used as a contact layer is sold under the trademark XEROFLO® by Kendall Corp., a division of Covidien.

Filler 38 may be arranged over contact layer 34 to fill wound "W" to the level of the surrounding healthy skin "s," or alternatively the wound "w" may be overfilled with filler 38. An absorbent material such as non-woven gauze or reticulated foam may be used for filler 38 to trap any exudate that migrates through contact layer 34. An antimicrobial dressing sold under the trademark KERLIX™ AMD™ by Kendall Corp., a division of Covidien, may be suitable for use as filler 38. To prevent adhesion to the wound "w," the filler 38 may also comprise a material configured such that its fibers do not tend to protrude through apertures of contact layer 34 where they may become engulfed by newly forming granulation tissue. One particular type of material exhibiting this characteristic is often referred to as "tow." The manufacturing process for synthetic fibers often includes an extrusion of an indeterminate length of continuous filaments, which are spun together to form fibers. Continuous lengths of un-spun filaments may be arranged in multi-strand bundles which are referred to as tow. A single length of tow formed from a hydrophobic material such as polyolefin may be laid in the wound bed "w" to form filler 38.

This arrangement allows for a complete removal of filler 50 when the dressing 16 is changed without re-injuring the wound "w."

Figure 2A:
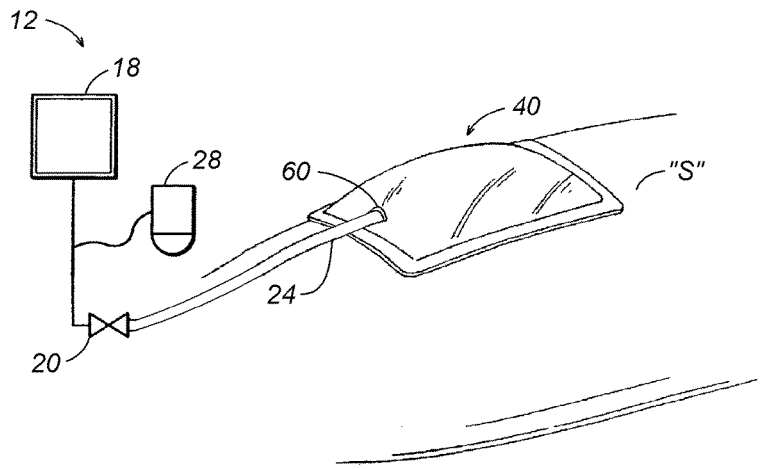
FIG. 2A is a perspective view of the vacuum wound therapy system of FIG. 1 assembled for use on a patient.
Figure 2B:
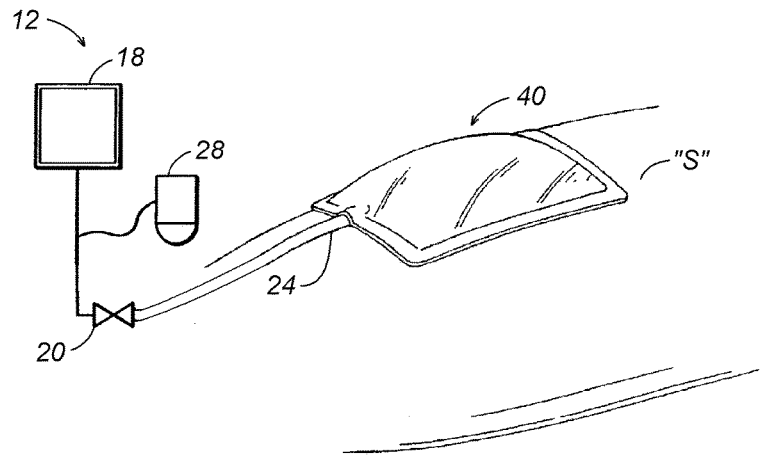
FIGS. 2B and 2C depict alternate assemblies of the vacuum wound therapy system.
Figure 2C:
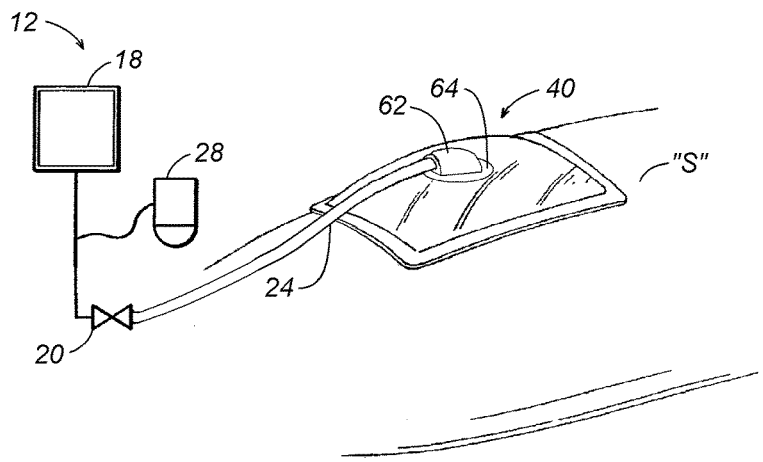

Cover layer 40 may be placed over the wound "W" enclosing the contact layer and filler therein. The periphery of cover layer 40 extends laterally beyond the perimeter of the wound bed "w" so as to contact the healthy skin "s" to form a seal over the wound "w." As depicted in FIG. 2A, an opening 60 may be provided or formed through the cover layer 40 to provide access for the vacuum tube 44 to communicate with the vacuum reservoir 14, or the vacuum tube 44 may be sealed under the periphery of the cover layer 40 as depicted in FIG. 2B. Alternatively, a distinct portal member or port 62 may be provided to facilitate fluid communication between the vacuum system 12 and the vacuum reservoir 14 as depicted in FIG. 2C. Port 62 may be configured as a rigid or semi rigid, low-profile component adapted to receive the vacuum tube 24 in a releasable and fluid-tight manner. The vacuum port 62 may be configured to include a wide and flexible flange 64 about its perimeter. The flange 64 permits an adhesive to be attached to either an underside of flange 64 for securement to an outer surface of cover layer 40, or to a top side of flange 64 to provide for mounting to the underside of the cover layer 40.

Figure 3B:
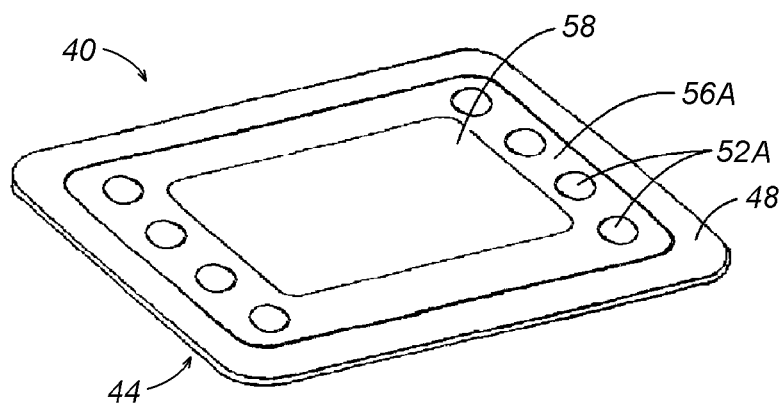
FIG. 3B depicts an alternate embodiment of the cover layer.

Referring now to FIG. 3A, cover layer 40 includes multiple performance zones 48, 52, 56 and 58 comprising various materials. A backing layer 44 may extend to the periphery of the cover layer 40 to provide a substrate for various coatings or materials defining the various performance zones 48, 52, 56 and 58. As depicted, each of the performance zones 48, 52, 56 and 58 is a continuous band arranged concentrically with respect to the others. The size, shape and position of the zones, however, may be varied according to the needs of the particular wound or treatment. For example, a cover layer 40A as depicted in FIG. 3B may be provided comprising a first intermediate zone 52 formed from a pattern of distinct shapes surrounded by second intermediate zone 56A. The various coatings may be laminated to the backing layer 44 or affixed by other appropriate means. The various materials forming layer 40 are described in greater detail herein below.

Backing layer 44 may be formed from a flexible polymeric membrane to act as a fluid barrier to allow for a sub-atmospheric pressure to be established in vacuum reservoir 14. The material's flexibility accommodates the pressure changes associated with the evacuation cycles in a VWT procedure. Backing layer 44 also serves as a microbial barrier preventing contaminants from entering the wound area. Preferably, the backing layer 44 is formed from a moisture vapor permeable membrane to promote the exchange of oxygen and moisture between the wound site and the atmosphere. A membrane that provides a sufficient moisture vapor transmission rate (MVTR) and is simultaneously impervious to liquid may be selected for use as backing layer 44. Another preferred membrane characteristic is the ability to stretch and conform to the compressed wound filler or wound bed. A membrane's tendency for elongation when subjected to a vacuum reduces the shear forces transitioned to the peri-wound area. One exemplary material for use in backing layer 44 is a transparent membrane sold under the trade name DURAFLEX® by Deerfield Urethan, a Bayer Material Science Company. Other materials which may be suitable for use in a backing layer include the thin films marketed under the names POLYSKIN®II by Kendall Corp., a division of Covidien, TEGADERM™ by 3M of St. Paul, Minn. and OPSITE™ by Smith and Nephew PLC of London, UK. A central zone 58 of the cover layer is defined by the area of the backing layer 44 not covered with any material which would tend to lessen the MVTR.

At the periphery of the cover layer 40 is a peripheral zone 48 defined by a continuous layer of high peal-strength, pressure sensitive adhesive. The adhesive forms a seal with the skin "s" around the perimeter of the cover layer to prevent the ingress of atmospheric fluids under the edges of the cover layer 40 when a reduced pressure is established in the reservoir 14. The adhesive defining the peripheral zone 48 is adapted to prevent the loss of adhesion to the skin even when exposed to environmental factors such as exudates from the wound "w" or body movements by the patient. In general, the high peal-strength adhesive is adapted to resist inadvertent lift-off, roll or "flagging," i.e., a failure of the dressing to adhere to itself, at the edges of the cover layer. The adhesive defining the peripheral zone 48 may include, for example, those adhesives included with the dressing sold under the trademark GELVA® Multipolymer Solutions by CYTEC Surface Specialties Inc.

Figure 4A:
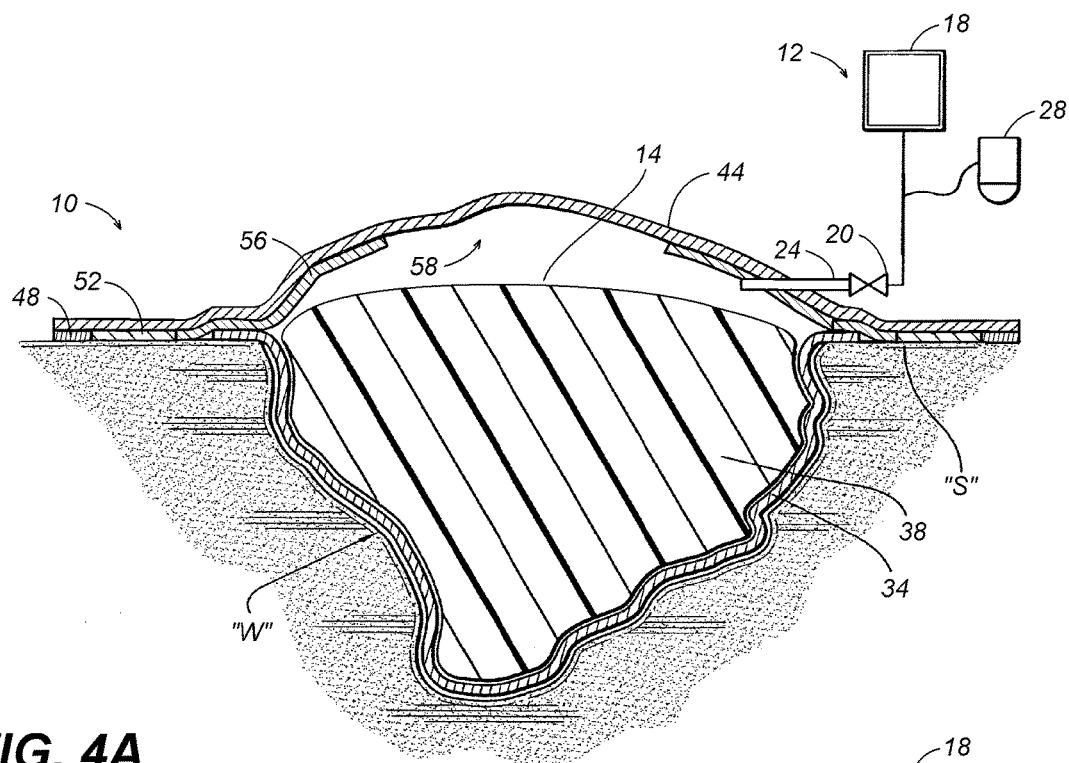
FIG. 4A is a cross sectional view of the vacuum wound therapy system of FIG. 1 in a first condition exhibiting a vacuum reservoir.
Figure 4B:
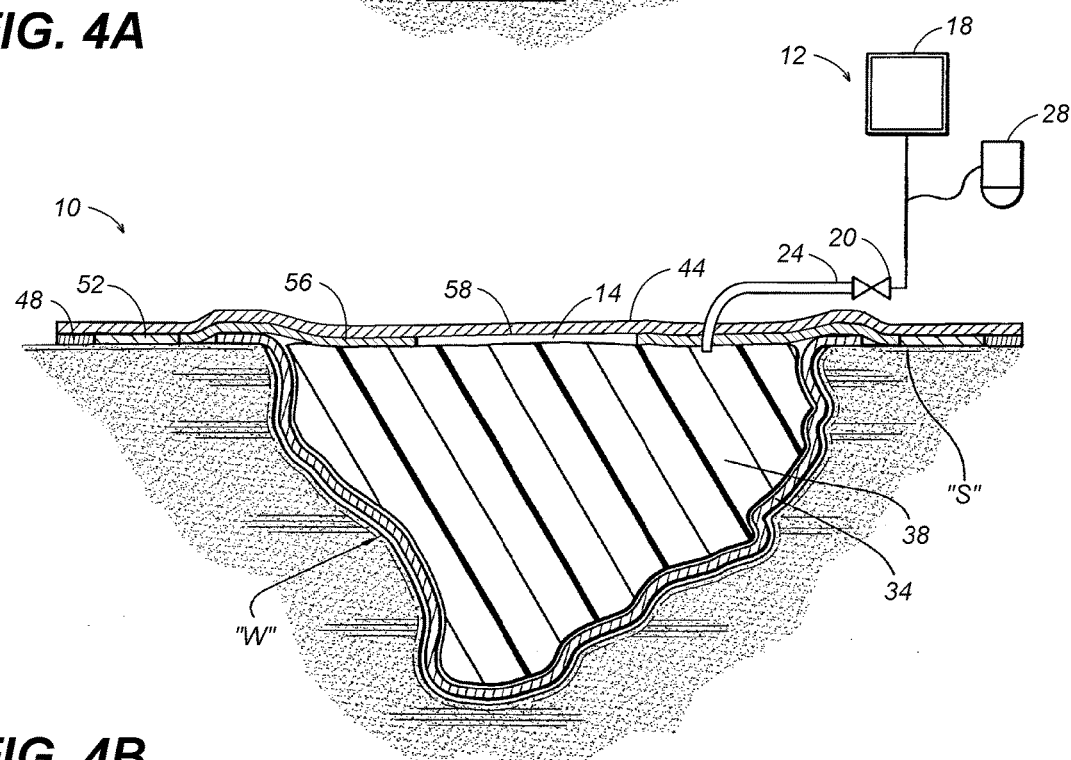
FIG. 4B depicts the vacuum wound therapy system in a second condition wherein the vacuum reservoir is evacuated.

The high peal-strength adhesive defining peripheral zone 48 may be bonded to backing layer 44, or applied directly to the skin "s" surrounding the wound bed "w." The adhesive should preferably be non-irritating and non-sensitizing to the contacted skin, and may be vapor moisture permeable to permit the contacted skin to transmit moisture. Preferably, the peripheral zone 48 and first intermediate zone 52 are positioned so as not to overlap the contact layer 34 as seen in FIGS. 4A and 4B. This arrangement facilitates the changing of certain individual components of the dressing, such as filler 38 without removing the entire dressing 16.

Disposed between the peripheral zone 48 and central zone 58 are first and second intermediate zones 52 and 56 respectively. First and second intermediate zones 52, 56 are defined by a layer of a substance for imparting a therapeutic effect or benefit to the wound "w." As indicated above, first and second intermediate zones 52, 56 may be arranged as continuous bands concentric with central zone 58 as seen in FIG. 3A, as a pattern of distinct shapes as seen in FIG. 3B, or any other convenient arrangement.

First intermediate zone 52 may, for example, be defined by a layer of an adhesive that laterally stabilizes the dressing when a reduced pressure is applied to evacuate the reservoir. As seen in FIG. 4B, when the reservoir is evacuated, the cover layer may tend to flatten against the wound "w." This may result in an outwardly directed force in the dressing 16 which may tend to separate the cover layer 40 from the skin "s." Also, the shear forces in the cover layer 40 may be transmitted to the skin "s," pulling apart newly forming granulation tissue and re-injuring the wound "w." To counteract these tendencies, a shear-resistant adhesive may be selected for use in first intermediate zone 52. Since many high peal-strength adhesives are adapted primarily to resist upwardly directed forces, i.e., those forces tending to lift the cover layer from the skin, a high peal-strength adhesive defining the peripheral zone 48 may be supplemented with an adhesive particularly adapted to resist lateral forces defining the first intermediate zone 52. A shear-resistant adhesive, such as GMS 1753 manufactured by CYTEC Surface Specialties Inc., that is moisture vapor permeable and suitable for use on the skin, may be used to define first intermediate zone 52.

Second intermediate zone 56 may be defined by a layer of a distinct material for providing a therapeutic effect or benefit to the wound. For example, second intermediate zone 56 may be adapted for transdermal medicament delivery. A substance such as an anti-infective agent, an antimicrobial, antibiotic, analgesic, healing factor, vitamins, growth factors, debridement agents or nutrients may be coated on portions of backing layer 108 to define second intermediate zone 56. Alternatively, a hydrogel may be selected for use in second intermediate zone 56 to maintain a moist wound environment. As seen in FIG. 4B, second intermediate zone 56 may be in contact with filler 38 when the reservoir 14 is evacuated to permit transfer beneficial agents thereto. Filler 38 and contact layer 34 may be eliminated if appropriate allowing for second intermediate zone 56 to contact the wound bed directly. It is also contemplated that an additional attachment adhesive may be beneficial for use in second intermediate zone 56.

Although the foregoing disclosure has been described in some detail by way of illustration and example, for purposes of clarity or understanding, it will be obvious that certain changes and modifications may be practiced within the scope of the appended claims.

What is claimed is:

1. A wound dressing for use with a negative pressure wound therapy apparatus, the wound dressing comprising:
    a cover layer comprising:
        a central zone comprising a moisture vapor permeable membrane devoid of any coating deterring the transmission of moisture through the membrane; and
        a peripheral zone positioned at a periphery of the cover layer, the peripheral zone comprising a first adhesive configured to form a seal with skin surrounding a wound;
    a filler configured to absorb wound exudate;
    an intermediate zone comprising a plurality of regions with a distinct shape and including a therapeutic material configured to provide a therapeutic effect to the wound, the intermediate zone further comprising a second adhesive configured to laterally stabilize the wound dressing when negative pressure is applied to the wound dressing, wherein the intermediate zone comprises a layer of material that is separate from the central zone and peripheral zone, and wherein the plurality of regions including the therapeutic material are arranged in the intermediate zone as a pattern; and
    a fluid flow passage configured to be in fluidic communication with the negative pressure wound therapy apparatus, the fluid flow passage configured to permit a one way flow of fluid away from the wound dressing when negative pressure is applied to the wound dressing;
    wherein the first adhesive is different from the second adhesive, and
    wherein the first adhesive comprises a high peal-strength adhesive and the second adhesive comprises a shear-resistant adhesive.

2. The dressing of claim 1, further comprising a port configured to be in fluid communication with the negative pressure wound therapy apparatus.

3. The dressing of claim 1, wherein the intermediate zone comprises a medicament delivery coating.

4. The dressing of claim 1, wherein the therapeutic material comprises at least one of anti-infective agent, antimicrobial, antibiotic, analgesic, healing factor, vitamins, growth factors, debridement agents, or nutrients.

5. The dressing of claim 1, wherein the cover layer comprises a flexible polymeric membrane that extends to the periphery of the cover layer, and the peripheral zone comprises the first adhesive bonded to the polymeric membrane.

6. The dressing of claim 1, wherein the filler comprises polyolefin filaments arranged in a multi-strand bundle.

7. The dressing of claim 1, wherein the filler comprises an absorbent material.

8. The dressing of claim 1, wherein the filler comprises a non-woven gauze or reticulated foam.

9. The dressing of claim 1, wherein the filler comprises an antimicrobial material.

10. The dressing of claim 1, wherein the distinct shape is circular and the plurality of regions including the therapeutic material are arranged around at least a portion of a periphery of the intermediate zone in a non-overlapping configuration.

11. The dressing of claim 1, wherein the fluid flow passage comprises a one way valve.

12. The dressing of claim 2, wherein the port is configured to permit attachment of the fluid flow passage.

* * * * *